(12) United States Patent
Cios (10) Patent No.: US 8,777,611 B2
(45) Date of Patent: Jul. 15, 2014

(54) ENHANCEMENT TO DENTAL ALIGNMENT DEVICE

(71) Applicant: Michele Cios, Boca Raton, FL (US)

(72) Inventor: Michele Cios, Boca Raton, FL (US)

(*) Notice: Subject to any disclaimer, the term of this patent is extended or adjusted under 35 U.S.C. 154(b) by 5 days.

(21) Appl. No.: 13/692,143

(22) Filed: Dec. 3, 2012

(65) Prior Publication Data

US 2013/0157224 A1 Jun. 20, 2013

Related U.S. Application Data

(60) Provisional application No. 61/577,796, filed on Dec. 20, 2011.

(51) Int. Cl.
*A61C 7/08* (2006.01)
*A61C 8/00* (2006.01)
*A61C 13/08* (2006.01)
*A61C 13/107* (2006.01)

(52) U.S. Cl.
CPC . *A61C 13/08* (2013.01); *A61C 7/08* (2013.01); *A61C 8/0019* (2013.01); *A61C 13/0001* (2013.01)
USPC .................................................................. 433/6

(58) Field of Classification Search
USPC ............................................. 433/6, 80; 128/861
See application file for complete search history.

(56) References Cited

U.S. PATENT DOCUMENTS

| | | | | |
|---|---|---|---|---|
| 3,505,995 A | * | 4/1970 | Greenberg | 128/862 |
| 5,573,399 A | * | 11/1996 | McClintock, II | 433/80 |
| 6,572,372 B1 | * | 6/2003 | Phan et al. | 433/6 |
| 6,607,382 B1 | * | 8/2003 | Kuo et al. | 433/6 |
| 6,790,035 B2 | * | 9/2004 | Tricca et al. | 433/6 |
| 8,070,485 B2 | * | 12/2011 | Schwartz et al. | 433/6 |
| 8,505,541 B2 | * | 8/2013 | Bardach et al. | 128/861 |
| 2008/0003541 A1 | * | 1/2008 | Leslie-Martin | 433/215 |
| 2008/0138767 A1 | * | 6/2008 | Kuo et al. | 433/167 |

* cited by examiner

*Primary Examiner* — Ralph Lewis
(74) *Attorney, Agent, or Firm* — Robert M. Downey, P.A.

(57) ABSTRACT

Systems and methods are disclosed for forming a pontic in a pontic-housing pocket of one or more polymeric shell appliances having teeth-receiving cavities. Cavities in the polymeric shell appliances corresponding to the location of a missing or extracted tooth may include a pontic-housing pocket. The pocket may be filled with a composite resin or acrylic material that hardens and presents with a similar visual appearance to a tooth, thereby presenting the illusion that there is no missing tooth. The pontic-hardening pocket may have a single opening of sufficient size for receiving a syringe for injecting the pontic material. After the material hardens and the pontic is formed, it is locked into the pocket, as it cannot fit through the single opening. As the space of a missing tooth is widened or narrowed by the alignment treatment, successive shell appliances may have pontics of successively larger or smaller size.

16 Claims, 6 Drawing Sheets

ENHANCEMENT TO DENTAL ALIGNMENT DEVICE

This non-provisional patent application is based on provisional patent application Ser. No. 61/577,796 filed Dec. 20, 2011.

BACKGROUND OF THE INVENTION

1. Field of the Invention

Some embodiments disclosed herein may relate to orthodontics and, more particularly, to dental alignment devices that support the use of pontics.

2. Discussion of the Related Art

Dental alignment devices provide a means for realigning teeth without the need for braces, which are universally seen as unaesthetic and inconvenient. Part of the aesthetic appeal of dental alignment devices is their transparency. While this feature is certainly considered desirable, it presents a problem to patients who are either missing a tooth or have had a tooth extracted in a dental procedure, who may understandably not want to have an unsightly gap in their dentition made visible.

To address this issue, the use of pontics in dental alignment devices has been created. Pontics are hardened materials that fill a gap in a dental alignment device and are colored to resemble a tooth. While the current use of pontics may in some cases adequately address the aesthetic issue of a missing tooth, it unfortunately introduces other unwanted issues.

The material currently used to create pontics can easily become brittle and then break and/or fall out of the gap, causing a severe inconvenience and even potential danger to a patient. Because of the hassles of creating a pontic matching a shade guide color, stocking the materials and avoiding the potential of the pontic falling out, some practitioners color in the pontic space with potentially toxic chemicals such as colored nail polish, or a similar substance. Using these chemicals can present an obvious health hazard to a patient, particularly since the patient is required to wear the alignment devices 22-23 hours a day. These issues routinely cause patients to require follow-up appointments to refill a pontic space, thereby costing both patients and practitioners extra time and lost revenues, in addition to the inconvenience of needing extra appointments.

In light of the severe shortcomings of the current practice of using pontics in dental alignment devices, there is an increasing need for an improved dental alignment device that provides a means for placing an aesthetic covering in an edentulous area without introducing any other potential hazards or inconveniences.

While certain aspects of conventional technologies have been discussed and presented to facilitate disclosure of some embodiments, Applicants in no way disclaim these technical aspects, and it is contemplated that the attached claims may encompass one or more of the conventional technical aspects discussed herein.

In this specification where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is it known to be relevant to an attempt to solve any problem with which this specification is concerned.

SUMMARY OF THE INVENTION

Some embodiments may address one or more of the problems and deficiencies discussed above. However, it is contemplated that some embodiments may prove useful in addressing other problems and deficiencies in a number of technical areas. Therefore the claims should not necessarily be construed as limited to addressing any of the particular problems or deficiencies discussed herein.

Some embodiments may disclose systems and methods for forming a pontic in a pontic-housing pocket of one or more polymeric shell appliances having teeth-receiving cavities. Cavities in the polymeric shell appliances corresponding to the location of a missing or extracted tooth may include a pontic-housing pocket. The pocket may be filled with a composite resin or acrylic material that hardens and presents with a similar visual appearance to a tooth, thereby presenting the illusion that there is no missing tooth. The pontic-hardening pocket may have a single opening of sufficient size for receiving a syringe for injecting the pontic material. After the material hardens and the pontic is formed, it is locked into the pocket, as it cannot fit through the single opening. The pocket can be filled by the practitioner or, alternatively, the manufacturer of the appliance can pre-fill the pocket according to a specified shade guide color. As the space of a missing tooth is widened or narrowed by the alignment treatment, successive shell appliances may have pontics of successively larger or smaller size.

One of the advantages provided by certain embodiments is that the pontic cannot fall out of the pontic-housing pocket even if it were to break, which saves patients the frustration, time, and money of making appointments to refill the pontic space.

These and other advantages of some embodiments are more readily apparent with reference to the detailed description and accompanying drawings.

BRIEF DESCRIPTION OF THE DRAWINGS

For a fuller understanding of the nature of some embodiments, reference should be made to the following detailed description taken in conjunction with the accompanying drawings in which.

Like reference numerals refer to like parts throughout the several views of the drawings.

DETAILED DESCRIPTION OF SOME EMBODIMENTS

The term "some" as used herein is defined as "none, or one, or more than one, or all." Accordingly, the terms "none," "one," "more than one," "more than one, but not all" or "all" would all fall under the definition of "some." The term "some embodiments" may refer to no embodiments or to one embodiment or to several embodiments or to all embodiments. Accordingly, the term "some embodiments" is defined as meaning "no embodiment, or one embodiment, or more than one embodiment, or all embodiments."

The terminology and structure employed herein is for describing, teaching and illuminating some embodiments and their specific features and elements and do not limit, restrict or reduce the spirit and scope of the claims or their equivalents.

More specifically, any terms used herein such as but not limited to "includes," "comprises," "has," "consists," and grammatical variants thereof do not specify an exact limitation or restriction and certainly do not exclude the possible addition of one or more features or elements, unless otherwise stated, and furthermore must not be taken to exclude the possible removal of one or more of the listed features and elements, unless otherwise stated with the limiting language "must comprise" or "needs to include."

All references herein to any features or elements of some embodiments such as but not limited to "a," "an," "one," "an additional," "another," or "the" feature or element, or grammatical variations thereof, unless otherwise specified by limiting language such as "only one . . . " wherein an exact number is specified along with the world "only" or "limited to", do not specifically prevent the inclusion or implementation of more than one of those features or elements, nor do they specifically admit that one or more of those features or elements must be used, unless otherwise specified by the limiting language "must have a" or "needs to include one."

All references herein including language such as but not limited to "one or more," "at least one," or grammatical variants thereof are nonlimiting and may be taken to mean that none of a certain feature or element may be used, or alternatively that only a singular feature or element may be used, or alternatively that only a plurality of elements or features may be used, or alternatively that either a singular or a plurality of features or elements may be used, or alternatively that none or one or more than one features or elements may be used. The use of this terminology herein does not specifically admit that more than one feature or element has to be used, nor does it specifically admit that only one feature or element has to be used, unless otherwise specified by the limiting language "must be more than" or "cannot be more than." Therefore, whether or not a certain feature or element were limited to being used only once, either way it may still be referred to as "one or more features" or "one or more elements" or "at least one feature" or "at least one element." Furthermore, the use of the terms "one or more" or "at least one" feature or element do not preclude there being none of that feature or element, unless otherwise specified by limiting language such as "there needs to be one or more . . . " or "one or more element is required."

Unless otherwise defined, all terms, and especially any technical and/or scientific terms, used herein may be taken to have the same meaning as commonly understood by one having an ordinary skill in the art.

Reference is made herein to some "embodiments." It should be understood that an embodiment is an example of a possible implementation of any features and/or elements presented in the attached claims. Some embodiments have been described for the purpose of illuminating one or more of the potential ways in which the specific features and/or elements of the attached claims fulfill the requirements of uniqueness, utility and non-obviousness.

Use of the phrases and/or terms such as but not limited to "a first embodiment," "a further embodiment," "an alternate embodiment," "one embodiment," "an embodiment," "multiple embodiments," "some embodiments," "other embodiments," or variants thereof do not necessarily refer to the same embodiments. For example, language such as "some embodiments include a feature" followed by "some embodiments include an element" does NOT necessarily admit that both of the feature and the element are included in all of the same embodiments.

Unless otherwise specified, one or more particular features and/or elements described in connection with one or more embodiments may be found in one embodiment, or may be found in more than one embodiment, or may be found in all embodiments, or may be found in no embodiments.

Although one or more features and/or elements may be described herein in the context of only a single embodiment, or alternatively in the context of more than one embodiment, or further alternatively in the context of all embodiments, the features and/or elements may instead be provided separately or in any appropriate combination or not at all. Conversely, any features and/or elements described in the context of separate embodiments may alternatively be realized as existing together in the context of a single embodiment.

Any and all details set forth herein are used in the context of some embodiments and therefore should not be necessarily taken as limiting factors to the attached claims. Any descriptions of elements and/or features and/or the materials used to create those elements or features, or examples or methods included in the descriptions of the various embodiments are nonlimiting and are given as an illustration only. Accordingly, the embodiments can be manufactured, distributed, used, practiced, and carried out in numerous ways.

The attached claims and their legal equivalents can be realized in the context of embodiments other than the ones used as illustrative examples in the description herein.

Referring to the several views of the drawings, the enhanced dental alignment device is shown in accordance with some embodiments. In each of these embodiments, the enhanced dental alignment device is generally indicated as 10.

Figure 1:
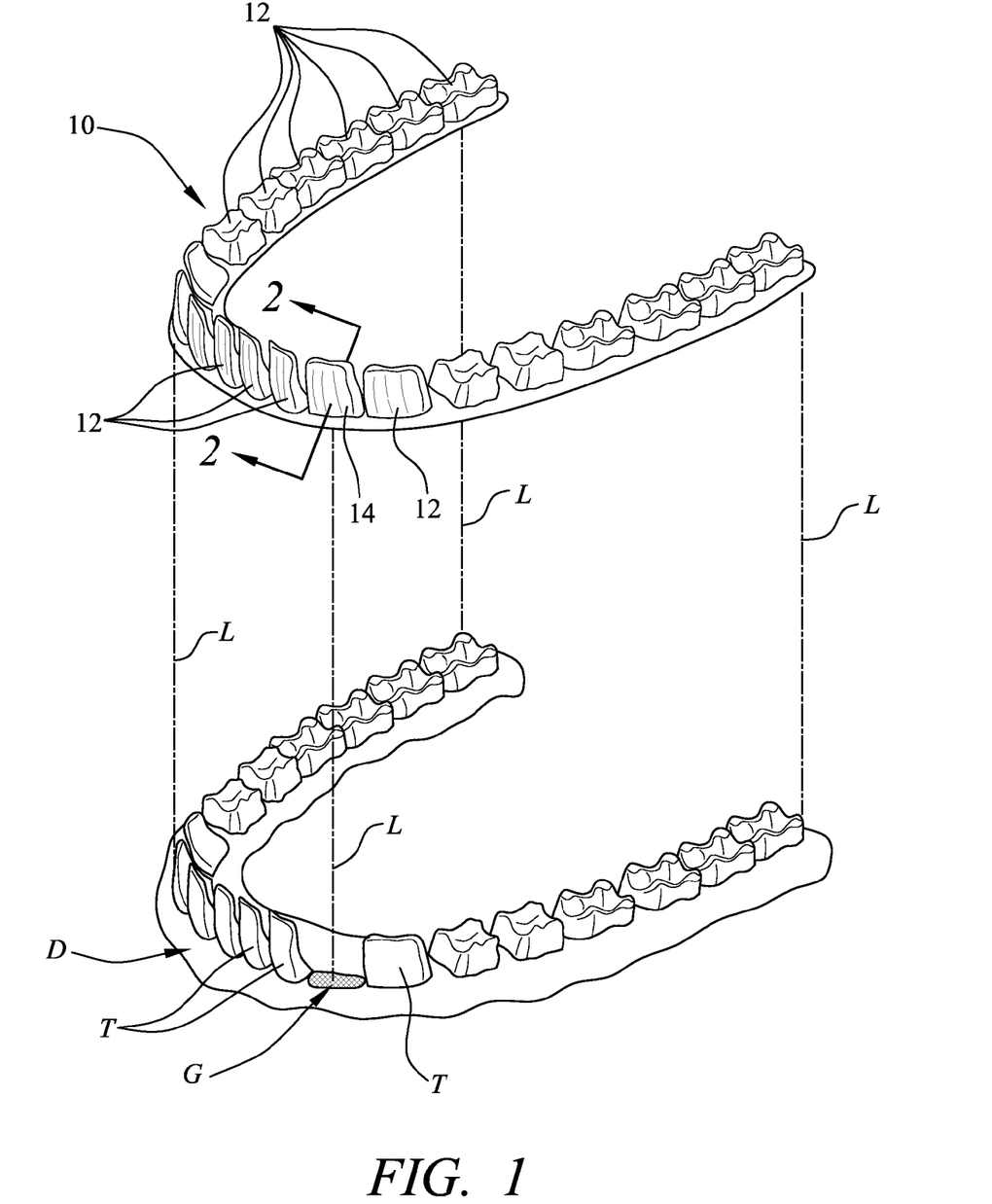
FIG. 1 is a perspective view of the enhanced dental alignment device according to an embodiment, wherein a patient's dentition is shown. Dotted lines indicated the direction of motion to put on and take off the enhanced dental alignment device.

Reference is now made to FIG. 1. The enhanced dental alignment device 10 is shown in position above a patient's dentition D constituting a tooth arrangement. Based on that patient's progress through a course of alignment treatment, the dentition D may constitute an initial tooth arrangement (i.e. before any treatment), an intermediate tooth arrangement (i.e. after some but not all treatment), or a final tooth arrangement (i.e. after treatment is complete). A course of treatment with the goal of realigning a patient's dentition D from an initial tooth arrangement to a final tooth arrangement will include the use of multiple enhanced dental alignment devices 10. These multiple devices 10 will have slight successive alterations made in order to slowly realign the dentition D. Any given enhanced dental alignment device 10 will correspond to one of the tooth arrangements, and as such will correspondingly be either a first appliance (i.e. corresponding to the initial tooth arrangement), an intermediate appliance (i.e. corresponding to one of the intermediate tooth arrangements), or a final appliance (i.e. corresponding to the final tooth arrangement). Dotted lines L indicate the direction of motion required to put on and take off the enhanced dental alignment device 10. According to some embodiments, the enhanced dental alignment device 10 may be used for a patient whose dentition D includes a gap G where a tooth is missing or has been extracted in a dental procedure.

Reference is still made to FIG. 1. The enhanced dental alignment device 10 may be a polymeric shell having teeth-receiving cavities 12 which corresponding to particular teeth T in the patient's dentition D. The enhanced dental alignment device 10 may further include one or more gap-covering cavities 14 corresponding to a gap G in the patient's dentition D. In some embodiments, the gap-covering cavities 14 will include a pontic-housing pocket (shown in the next Figures) in order to aesthetically cover the gap G which might otherwise be unsightly through the transparent dental alignment device 10.

Figure 2:
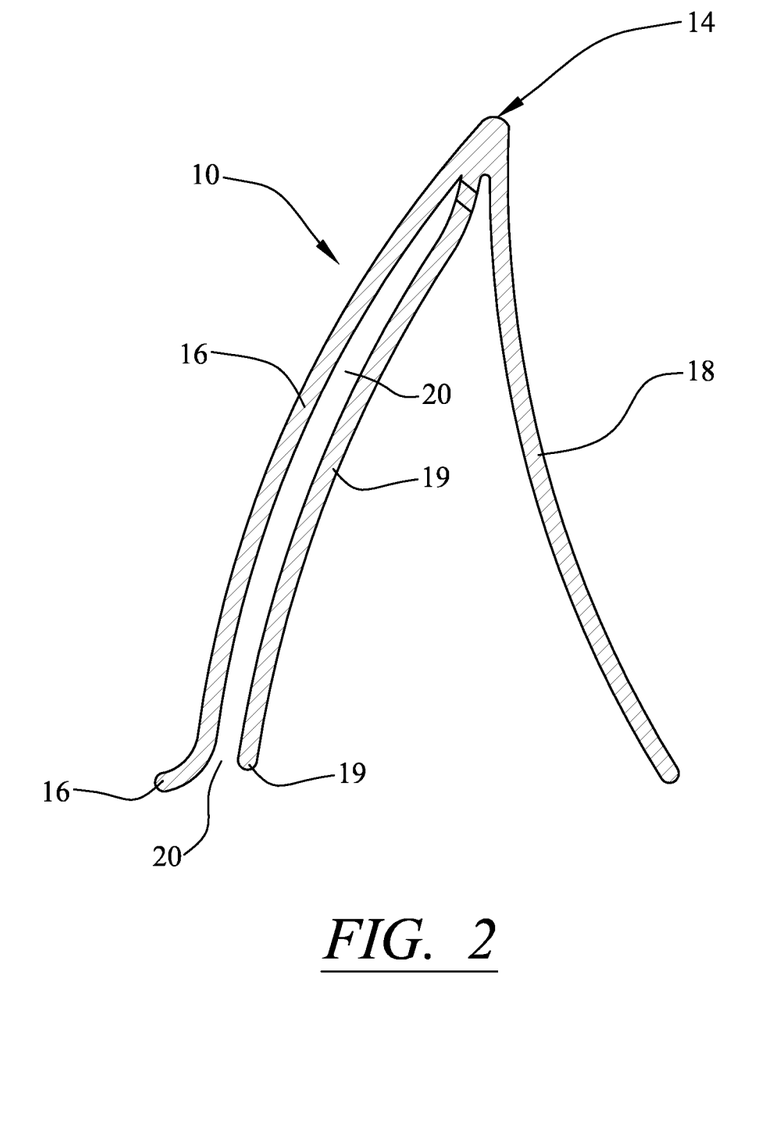
FIG. 2 is a cross-sectional view taken along the line A1-A1 in FIG. 1 of the enhanced dental alignment device according to an embodiment.

Additional reference is now made to FIG. 2. A cross section of the gap-covering cavity 14 taken along the line A1-A1 in FIG. 1 is shown. The gap-covering cavity 14 includes two primary outer surfaces: a frontal outer surface 16 and a rear outer surface 18. The term "frontal" in this reference specifically means towards the exterior of the mouth, or along the convex side of the dentition, while "rear" indicates a direction towards a patients tongue or throat, or along the concave side of the dentition. Please note that the frontal and rear outer surfaces 16 and 18 may be included in all teeth-receiving cavities 12 as well as any gap-covering cavities 14. The gap-covering cavity further includes a pocket-forming wall 19 which creates a pontic-housing pocket 20. The pontic-housing pocket 20 is therefore adjacent to the frontal outer surface 16 and runs adjacent along the entirety of the frontal outer surface 16.

Figure 3:
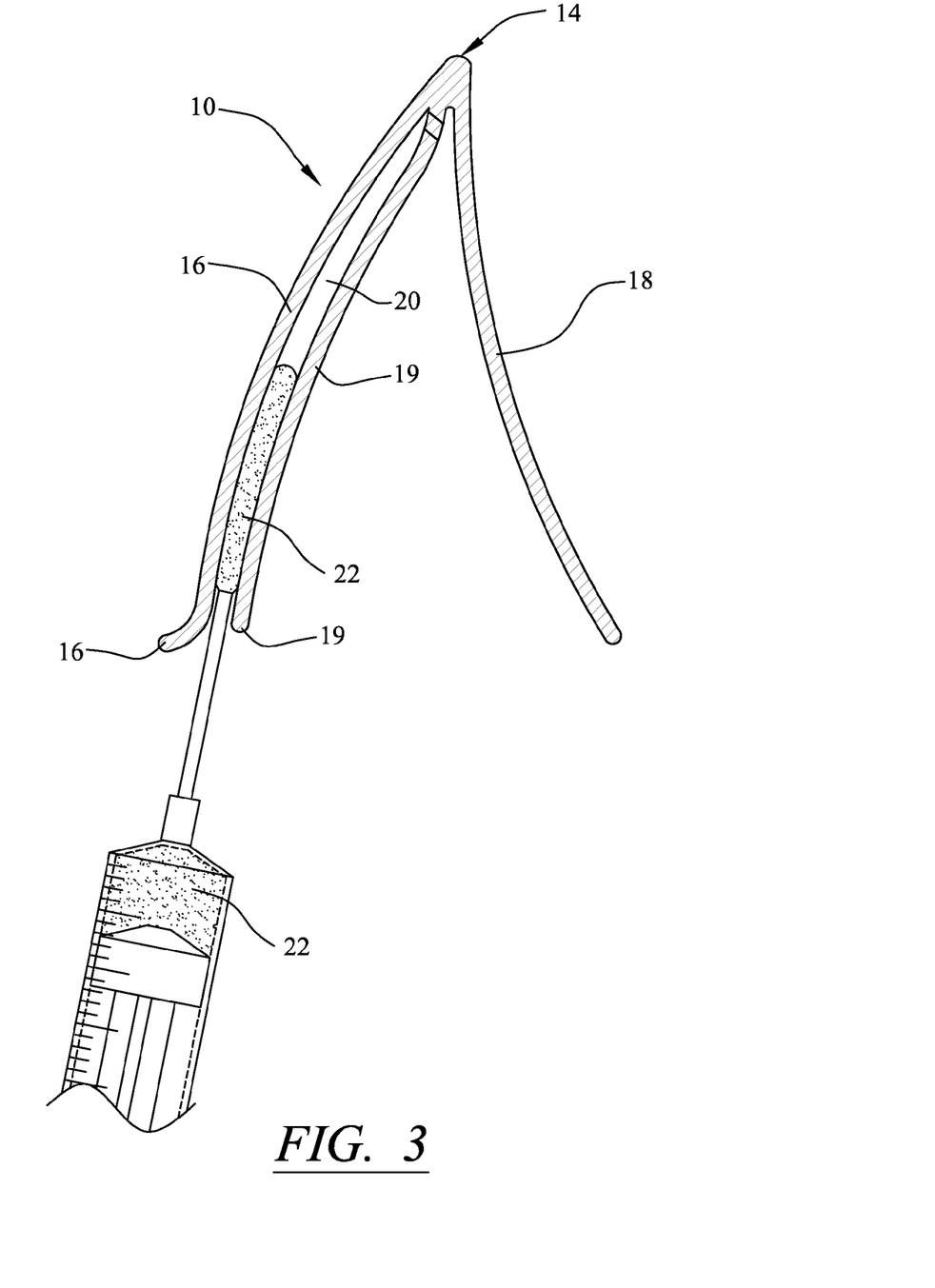
FIG. 3 is a cross-sectional view of the enhanced dental alignment device according to the embodiment of FIG. 2 illustrating a syringe being used to fill in the pontic-housing pocket with the pontic-forming material.

Additional reference is now made to FIG. 3. A pontic-forming material 22 will be inserted into the pontic-housing pocket 20 through use of a syringe S or other means. The pontic-forming material 22 may be a composite resin or acrylic material, or other suitable material or combination of materials. The pontic-forming material 22 will fill the entirety of the pontic-housing pocket 20. It is noted that the pocket may be filled in this manner at a practitioner's office or, alternatively, the manufacturer of the alignment device can pre-fill the pocket(s) according to a specified shade guide color to match the patient's teeth.

Figure 4:
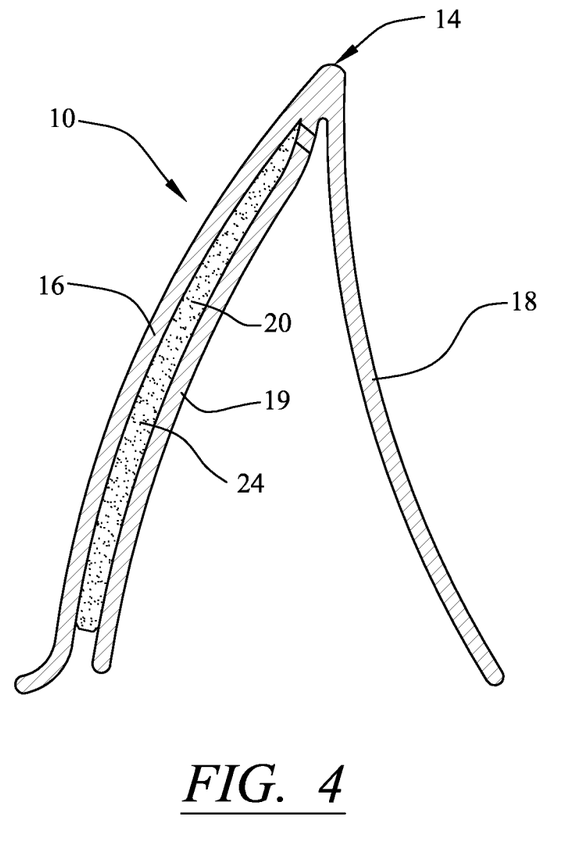
FIG. 4 is a cross-sectional view of the enhanced dental alignment device according to the embodiment of FIG. 3 illustrating the completed pontic in the pontic-housing pocket.

Additional reference is now made to FIG. 4. After the pontic-forming material 22 shown in FIG. 3 has hardened, a pontic 24 is formed. The pontic 24 is a visual substitute for a tooth T, such that when the enhanced dental alignment device 10 is worn over a patient's dentition D including a toothless gap G, the pontic 24 will appear to be a tooth T located at the gap G such that viewers of the patient's dentition will not be able to tell that an unsightly gap G exists. In order to achieve this illusion, the pontic 24 is made to be a substantially similar color and size of the tooth that would normally be in the gap G.

Figure 5:
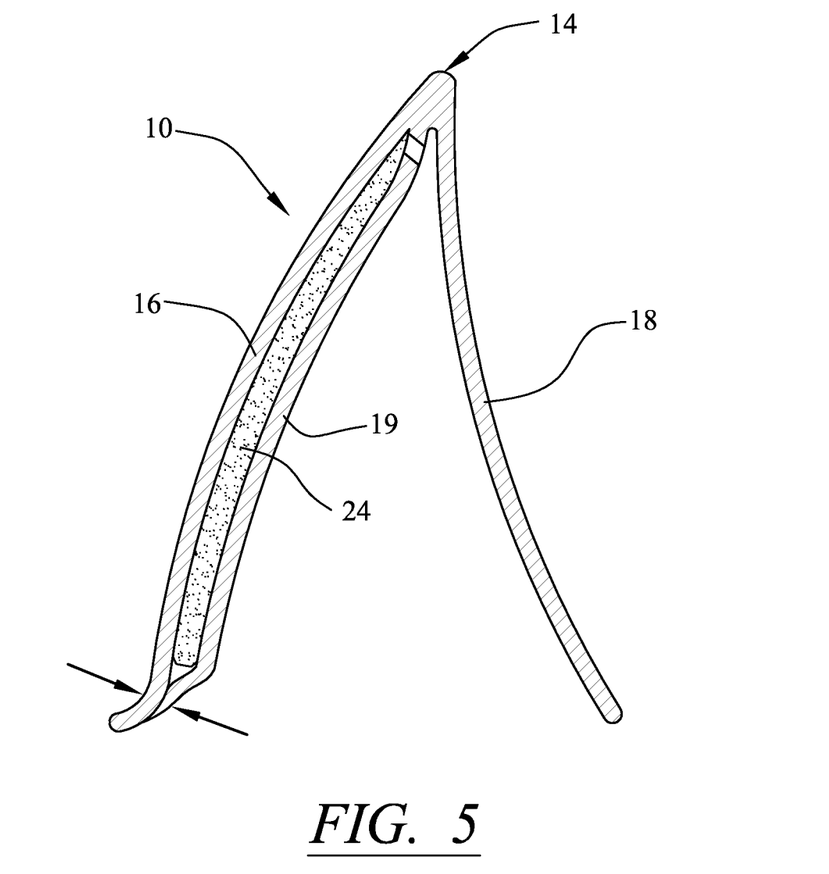
FIG. 5 is a cross-sectional view of the enhanced dental alignment device according to an embodiment wherein the pontic-housing pocket is at least partially closed after the formation of the pontic therein in order to prevent the pontic therein from falling out of the pontic-housing pocket.

Additional reference is now made to FIG. 5. After the pontic 24 has been formed as seen in FIG. 4, it may be desirable to close the pontic-forming pocket 20 such that the pontic 24 can no longer withdraw from the pocket 20. This can be seen here in FIG. 5 as the pocket-forming wall 19 is partially bent to become closer and/or connect to the frontal outer surface 16. There are other methods of closing the pontic-forming pocket 20 as well. Such methods may include molding the pocket 20 such that its opening is large enough to admit the entry of the tip of the syringe S for injecting the pontic-forming material, but too small to allow the pontic 24 to withdraw from the pocket 20. The specifics of this type of method are limitless, and as such any method which performs this is fully considered and envisioned within the spirit and scope of the attached claims.

Figure 6:
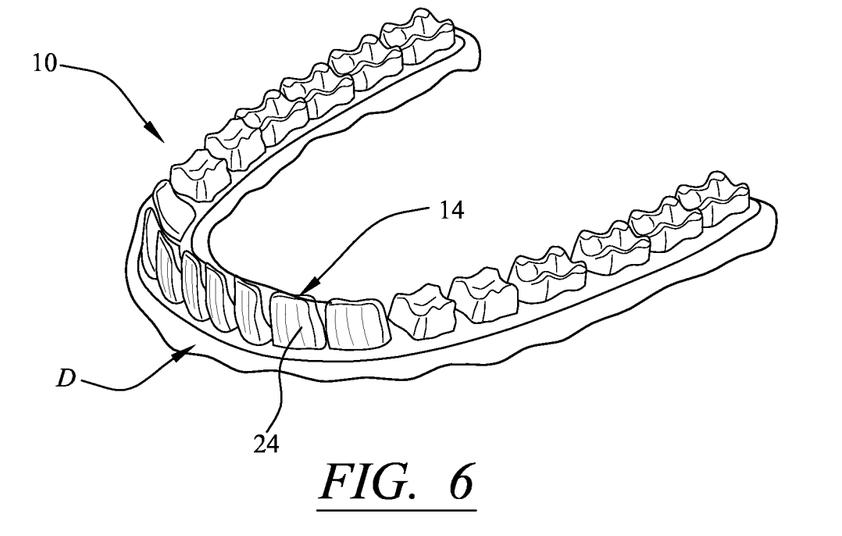
FIG. 6 is a perspective view of the enhanced dental alignment device according to an embodiment wherein the device has a pontic in at least one pontic-housing pocket and is in place over a patient's dentition.

Additional reference is now made to FIG. 6. The enhanced dental alignment device 10 can be seen in place over a patient's dentition D. The pontic 24 has a similar color and overall appearance as a real tooth T, and therefore covers the unsightly gap G where a tooth is missing. A patient using the enhanced dental alignment device 10 may realign his or her teeth without the inconvenience of displaying the gap G.

Figure 7:
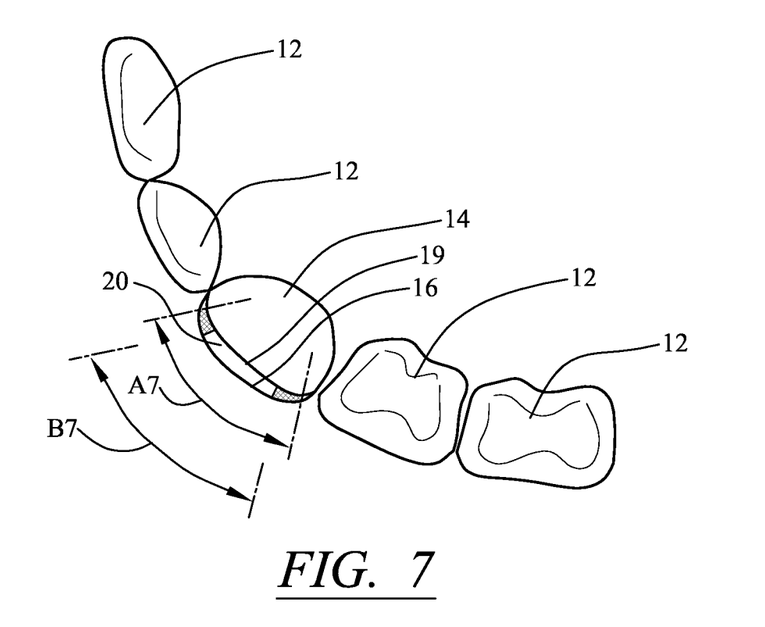
FIG. 7 is a bottom plan view of the enhanced dental alignment device according to an embodiment wherein the pontic-housing pocket is shown to have an opening with a smaller width than the width of the pocket itself, thereby preventing a pontic from leaving the pocket once formed.

Additional reference is now made to FIG. 7. The dental alignment device 10 is shown from below with more details of the pontic-housing pocket 20 being identified. Specifically, the pontic-housing pocket 20 has an opening formed between the frontal outer surface 16 and the pocket-forming wall 19. The pocket 20 has a width identified by letter A7. This is the same width as the pontic 24 that will eventually be formed in the pocket 20. However, the opening may have a smaller width, identified by the arrow B7, such that a pontic having a width of A7 would be unable to fit through the opening having a width of B7, thereby locking the pontic 24 into the pocket 20. Because dental aligners 10 are temporary and are replaced often, it may be advantageous to have the pontic 24 completely locked into the pocket 20 such that is cannot be removed.

Additional embodiments and utilities of the enhanced dental alignment device 10 are considered and understood. For instance, dental alignment devices are common among children. Since each individual dental alignment device is only worn for a short period (i.e. a couple weeks) before the next successive device is worn, the use of pontics 24 may allow the use of a "themed" dental alignment device 10. For instance, pontics 24 could be placed in all of the teeth-receiving cavities 12 and could be colored a certain way, such as alternating red white and blue for around the Fourth of July. Such a possibility exists because of the nature of the short duration of wearing the device. As such, although one of the highlighted features of the pontic 24 is its ability to cover up a gap G where a tooth is missing, there are indeed other aesthetic reasons why it may be used as well, all of which are envisioned and considered within the spirit and scope of the attached claims.

Throughout the detailed description and the accompanying drawings enclosed herein, some embodiments have been shown, described and detailed, wherein a variety of possible elements and/or features may be formed and configured in different ways. Accordingly, any and all possible combinations of the elements and/or features described in accordance with these various embodiments may be desirable to manufacturers and/or may help to more successfully meet customers' specific needs and/or preferences. Consequently, any and all possible combinations of the features or elements of one embodiment or more than one embodiment or all embodiments mentioned herein are fully considered within the spirit and scope of the attached claims and their legal equivalents.

Thus, some embodiments of an enhanced dental alignment device have been disclosed. Other embodiments are contemplated and envisioned, and therefore it is recognized that departures from the embodiments described in this disclosure may certainly exist within the spirit and scope of the attached claims and their legal equivalents. Those having an ordinary skill in the will envision other possible variations and modifications to features and/or elements of the embodiments, and they will envision other possible embodiments, all of which may fall within the spirit and scope of the attached claims.

The spirit and scope of the attached claims is therefore not limited by the descriptions and illuminations of the embodiments that have already been presented, but rather the spirit and scope can only be defined by the attached claims and their legal equivalents as interpreted under the doctrine of equivalents. Variations, alternatives, adjustments, modifications, tunings, and deviations from the embodiments of the instant disclosure are fully contemplated and envisioned within the spirit and scope of the attached claims.

What is claimed is:

1. A system for repositioning the teeth of a user from an initial tooth arrangement to a final tooth arrangement, and said system comprising:
   a first polymeric shell having a plurality of teeth-receiving cavities sized and configured to reposition the teeth from the initial tooth arrangement to a first intermediate tooth arrangement;
   at least one intermediate polymeric shell having a plurality of teeth-receiving cavities sized and configured to progressively reposition the teeth from the first intermediate tooth arrangement to at least one successive intermediate tooth arrangement;
   a final polymeric shell having a plurality of teeth-receiving cavities sized and configured to reposition the teeth from the at least one successive intermediate tooth arrangement to a final tooth arrangement;
   a pontic-housing pocket on at least one of said plurality of teeth-receiving cavities, and said pontic-housing pocket being formed between a frontal outer wall of the cavity and a pocket-forming wall located adjacent to the frontal outer wall and in the interior of the cavity, and whereby an opening between the frontal outer wall and the pocket-forming wall provides access into said pontic-housing pocket;
   a pontic-forming material;
   wherein said pontic-housing pocket is structured and disposed for receiving the pontic-forming material through the opening on said pontic-housing pocket, and said frontal outer wall and said pocket-forming wall being structured to contain and captivate the pocket-forming material within said pocket-housing, and whereby the pontic-forming material hardens into a pontic after being received in said pontic-housing pocket; and
   wherein the opening between the frontal outer wall and the pocket-forming wall is smaller than the hardened pontic in said pontic-housing pocket, thereby preventing removal of said pontic through the opening.

2. The system for repositioning the teeth of a user as recited in claim 1 wherein the pontic-forming material is selected to match the color of the user's teeth.

3. The system for repositioning the teeth of a user as recited in claim 1 wherein said first polymeric shell, said at least one intermediate polymeric shell, and said final polymeric shell are transparent.

4. The system for repositioning the teeth of a user as recited in claim 1 wherein said frontal outer wall is transparent.

5. The system for repositioning the teeth of a user as recited in claim 1 wherein the pontic-forming material comprises a composite resin.

6. The system for repositioning the teeth of a user as recited in claim 1 wherein the pontic-forming material comprises an acrylic material.

7. A system for repositioning the teeth of a user from an initial tooth arrangement to a final tooth arrangement, and said system comprising:
   a polymeric shell having a plurality of teeth-receiving cavities sized and configured to reposition the teeth from the initial tooth arrangement to a secondary tooth arrangement;
   a pontic-housing pocket on at least one of said plurality of teeth-receiving cavities, and said pontic-housing pocket being formed between a frontal outer wall of the cavity and a pocket-forming wall located adjacent to the frontal outer wall and in the interior of the cavity, and whereby an opening between the frontal outer wall and the pocket-forming wall provides access into said pontic-housing pocket;
   a pontic-forming material;
   wherein said pontic-housing pocket is structured and disposed for receiving the pontic-forming material through the opening on said pontic-housing pocket and said frontal outer wall and said pocket-forming wall being structured to contain and captivate the pocket-forming material within said pocket-housing, and whereby the pontic-forming material hardens into a pontic after being received in said pontic-housing pocket; and
   wherein the opening between the frontal outer wall and the pocket-forming wall is smaller than the hardened pontic in said pontic-housing pocket, thereby preventing removal of said pontic through the opening.

8. The system for repositioning the teeth of a user as recited in claim 7 wherein the pontic-forming material is selected to match the color of the user's teeth.

9. The system for repositioning the teeth of a user as recited in claim 7 wherein said polymeric shell is transparent.

10. The system for repositioning the teeth of a user as recited in claim 7 wherein said frontal outer wall is transparent.

11. The system for repositioning the teeth of a user as recited in claim 7 wherein the pontic-forming material comprises a composite resin.

12. The system for repositioning the teeth of a user as recited in claim 7 wherein the pontic-forming material comprises an acrylic material.

13. A system for repositioning the teeth of a user from an initial tooth arrangement to a final tooth arrangement, and said system comprising:
   a transparent polymeric shell having a plurality of teeth-receiving cavities sized and configured to reposition the teeth from the initial tooth arrangement to a secondary tooth arrangement;
   a pontic-housing pocket on at least one of said plurality of teeth-receiving cavities, and said pontic-housing pocket being formed between a transparent frontal outer wall of the cavity and a pocket-forming wall located adjacent to the transparent frontal outer wall and in the interior of the cavity, and whereby an opening between the transparent frontal outer wall and the pocket-forming wall provides access into said pontic-housing pocket;
   a pontic-forming material;
   wherein said pontic-housing pocket is structured and disposed for receiving the pontic-forming material through the opening on said pontic-housing pocket and said frontal outer wall and said pocket-forming wall being structured to contain and captivate the pocket-forming material within said pocket-housing, and whereby the pontic-forming material hardens into a pontic after being received in said pontic-housing pocket; and
   wherein the opening between the transparent frontal outer wall and the pocket-forming wall is smaller than the hardened pontic in said transparent pontic-housing pocket, thereby preventing removal of said pontic through the opening.

14. The system for repositioning the teeth of a user as recited in claim 13 wherein the pontic-forming material is selected to match the color of the user's teeth.

15. The system for repositioning the teeth of a user as recited in claim 13 wherein the pontic-forming material comprises a composite resin.

16. The system for repositioning the teeth of a user as recited in claim 13 wherein the pontic-forming material comprises an acrylic material.

* * * * *